US012611094B2

(12) United States Patent
Onobori

(10) Patent No.: US 12,611,094 B2
(45) Date of Patent: Apr. 28, 2026

(54) PHOSPHOR ILLUMINATION SYSTEM FOR ENDOSCOPIC IMAGING

(71) Applicant: HOYA CORPORATION, Tokyo (JP)

(72) Inventor: Kunihiko Onobori, Friedberg (DE)

(73) Assignee: HOYA CORPORATION, Tokyo (JP)

( * ) Notice: Subject to any disclaimer, the term of this patent is extended or adjusted under 35 U.S.C. 154(b) by 403 days.

(21) Appl. No.: 18/274,273

(22) PCT Filed: Nov. 12, 2021

(86) PCT No.: PCT/IB2021/060488
§ 371 (c)(1),
(2) Date: Jul. 26, 2023

(87) PCT Pub. No.: WO2022/162454
PCT Pub. Date: Aug. 4, 2022

(65) Prior Publication Data
US 2024/0081632 A1     Mar. 14, 2024

(30) Foreign Application Priority Data

Jan. 27, 2021    (DE) ..................... 10 2021 101 832.3

(51) Int. Cl.
*A61B 1/06*          (2006.01)
*A61B 1/00*          (2006.01)
(Continued)

(52) U.S. Cl.
CPC ........ *A61B 1/0653* (2013.01); *A61B 1/00096* (2013.01); *A61B 1/041* (2013.01); *A61B 1/07* (2013.01)

(58) Field of Classification Search
None
See application file for complete search history.

(56) References Cited

U.S. PATENT DOCUMENTS

2009/0167149 A1* 7/2009 Ito ........................ G02B 6/0008
                                                      313/501
2009/0203966 A1* 8/2009 Mizuyoshi ......... A61B 1/00096
                                                      600/182
(Continued)

FOREIGN PATENT DOCUMENTS

EP        2482349 A1    8/2012
EP        2952132 A1    12/2015
(Continued)

OTHER PUBLICATIONS

Office Action issued in Japanese Patent Application No. 2023-533779, dated Apr. 2, 2024, together with an English translation.
(Continued)

*Primary Examiner* — John P Leubecker
(74) *Attorney, Agent, or Firm* — GREENBLUM & BERNSTEIN, P.L.C.

(57)                ABSTRACT

An endoscope includes a phosphor layer, and a light output layer; wherein the light output layer emits a first excitation light and a second excitation light to illuminate an object space, through the phosphor layer, with first and second combined light, an intensity of the first excitation light has an absolute maximum at a first peak wavelength, an intensity of the second excitation light has an absolute maximum at a second peak wavelength different from the first peak wavelength, the phosphor layer comprises one or more phosphors, each of the one or more phosphors is configured to be excited by the first excitation light to generate first excited light of the respective phosphor, each of the one or more phosphors is configured to be excited by the second excitation light to generate second excited light of the respective phosphor.

21 Claims, 11 Drawing Sheets

(51) Int. Cl.
*A61B 1/04* (2006.01)
*A61B 1/07* (2006.01)

(56) References Cited

U.S. PATENT DOCUMENTS

| | | | | |
|---|---|---|---|---|
| 2009/0306478 A1* | 12/2009 | Mizuyoshi | ............... | A61B 1/07 |
| | | | | 600/178 |
| 2009/0312607 A1* | 12/2009 | Sunagawa | ............ | A61B 5/0084 |
| | | | | 348/370 |
| 2010/0286475 A1* | 11/2010 | Robertson | .......... | A61B 1/00188 |
| | | | | 600/109 |
| 2011/0034770 A1* | 2/2011 | Endo | ...................... | A61B 1/063 |
| | | | | 600/118 |
| 2011/0172492 A1* | 7/2011 | Erikawa | ................... | A61B 1/07 |
| | | | | 600/178 |
| 2011/0237894 A1* | 9/2011 | Ozawa | ............... | A61B 1/00188 |
| | | | | 600/168 |
| 2011/0273548 A1 | 11/2011 | Uchiyama et al. | | |
| 2012/0008318 A1* | 1/2012 | Ishiwata | ................ | H05B 45/20 |
| | | | | 362/231 |
| 2012/0197077 A1* | 8/2012 | Kaku | ............... | A61B 1/000094 |
| | | | | 600/109 |
| 2012/0200687 A1* | 8/2012 | Kikuchi | ............... | A61B 1/0653 |
| | | | | 348/370 |
| 2013/0113906 A1* | 5/2013 | Saito | ................ | A61B 1/000094 |
| | | | | 348/E7.085 |
| 2015/0327755 A1 | 11/2015 | Daidoji et al. | | |
| 2015/0374217 A1* | 12/2015 | Sinofsky | ................... | F21K 2/00 |
| | | | | 600/177 |
| 2018/0216002 A1* | 8/2018 | Nagao | .................... | H04N 23/10 |
| 2019/0110672 A1* | 4/2019 | Onobori | ............... | A61B 1/0684 |
| 2023/0082243 A1 | 3/2023 | Onobori | | |
| 2023/0280001 A1 | 9/2023 | Onobori et al. | | |

FOREIGN PATENT DOCUMENTS

| | | |
|---|---|---|
| JP | 2014-144144 A | 8/2014 |
| WO | WO 2010/143692 A1 | 12/2010 |

OTHER PUBLICATIONS

International Search Report issued in WIPO Patent Application No. PCT/IB2021/060488, dated Jan. 21, 2022.

* cited by examiner

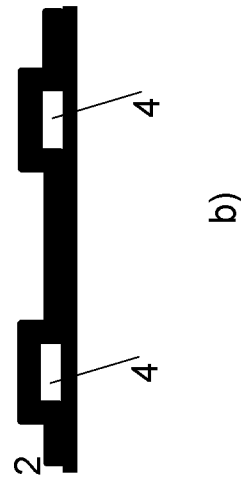
b)
Fig. 6
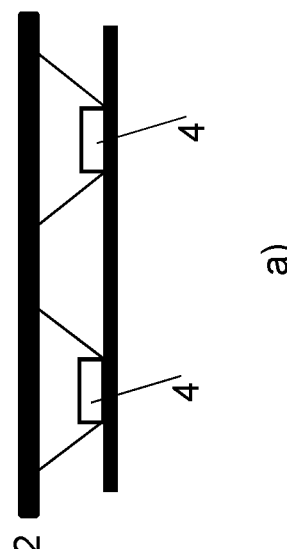
a)

a)

b)

PHOSPHOR ILLUMINATION SYSTEM FOR ENDOSCOPIC IMAGING

FIELD OF THE INVENTION

The present application is related to an illumination system for endoscopic imaging. In particular, the illumination system comprises a phosphor.

BACKGROUND OF THE INVENTION

To emphasize clinical information, spectral illumination of targeting molecules which have optical properties in human body, such as haemoglobin and autofluorescence molecules like lipofuscin, is used in medical imaging and, in particular, in endoscopy.

As an example, FIG. 1 shows the absorption spectra of oxygenated haemoglobin (HbO2) and deoxygenated haemoglobin (Hb), which both have a respective first absorption peak in the wavelength range between 400 and 450 nm. A second absorption peak (green spectrum) is in a range of 520 nm to 590 nm.

The difference in the absorption is utilised to visualise bleeding point during treatment procedure. E.g. using green, amber and red spectrum, highest absorption comes from green spectrum, second highest absorption is amber and lowest one is red. Thus, bleeding point is visualised together with other biomedical information.

Also, some imaging agents, such as ICG (indocyanine green), AF488, and IRdye family, may be applied for fluorescence imaging and sometimes for phototherapy like PDT (photodynamic therapy) and PIT (photo immuno-therapy).

Since the molecules and imaging agents have their absorption/excitation and emission characteristics, a suitable spectral illumination is desirable for illumination optics and light source. Furthermore, to acquire emission light with a good signal-noise ratio from these molecules and imaging agents, special objective optics are typically used. Often, they comprise an excitation light cut filter or equivalent optics.

However, when it comes to endoscopy, white light imaging is typically required, too, such that endoscopes typically comprise an option for white light illumination (WLI). Since the space available for the light source(s) is small in an endoscope, especially when the light source is embedded inside the endoscope side, possible arrangements are limited.

SUMMARY OF THE INVENTION

It is provided a rigid tip portion of an endoscope or a capsule endoscope according to claim 1. Furthermore, there are provided an endoscope and an endoscope system employing the rigid tip portion of claim 1, as defined by the respective claims. Still furthermore, there is provided an endoscope system as defined by the respective independent claim.

The rigid tip portion and the capsule endoscope, respectively, allow to provide both spectral illumination (e.g. for vascular imaging) and WLI, while only limited space is needed. Furthermore, since all the phosphors of the phosphor layer contribute to both spectral illumination and WLI, efficiency of the illumination is enhanced. In some embodiments, the spectral shape of the illumination may be tuned.

BRIEF DESCRIPTION OF THE DRAWINGS

FIG. 6 shows cross-sections through some example illumination systems;

DETAILED DESCRIPTION OF CERTAIN EMBODIMENTS

Herein below, certain embodiments of the present invention are described in detail as reference to the accompanying drawings, wherein the features of the embodiments can be freely combined with each other unless otherwise described. However, it is to be expressly understood that the description of certain embodiments is given by way of example only, and that it is by no means intended to be understood as limiting the invention to the disclosed details.

In the Figures, the same numerals designate corresponding components, which are distinguished by different letters. The Figures are schematic only. In particular, the sizes are not at scale.

Figure 1:
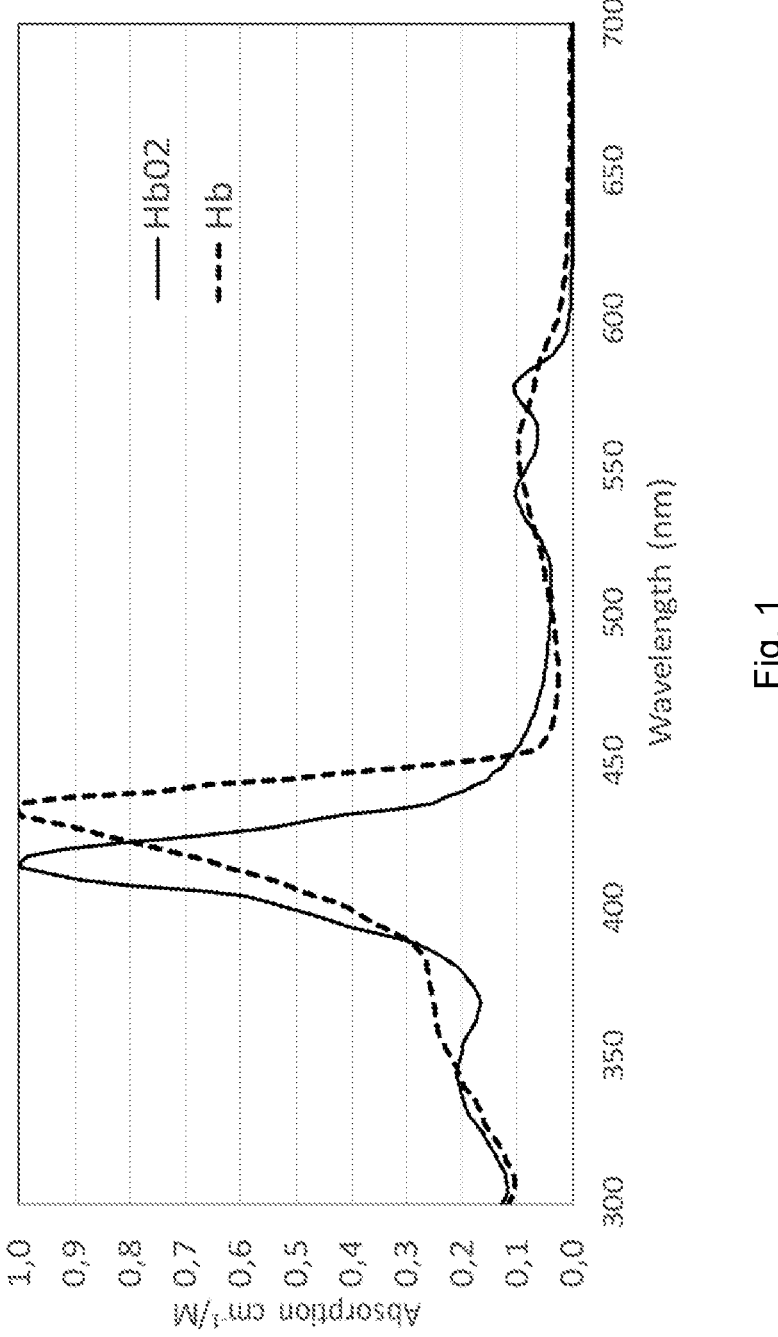
FIG. 1 shows absorption spectra of oxygenated haemoglobin and deoxygenated haemoglobin.
Figure 2:
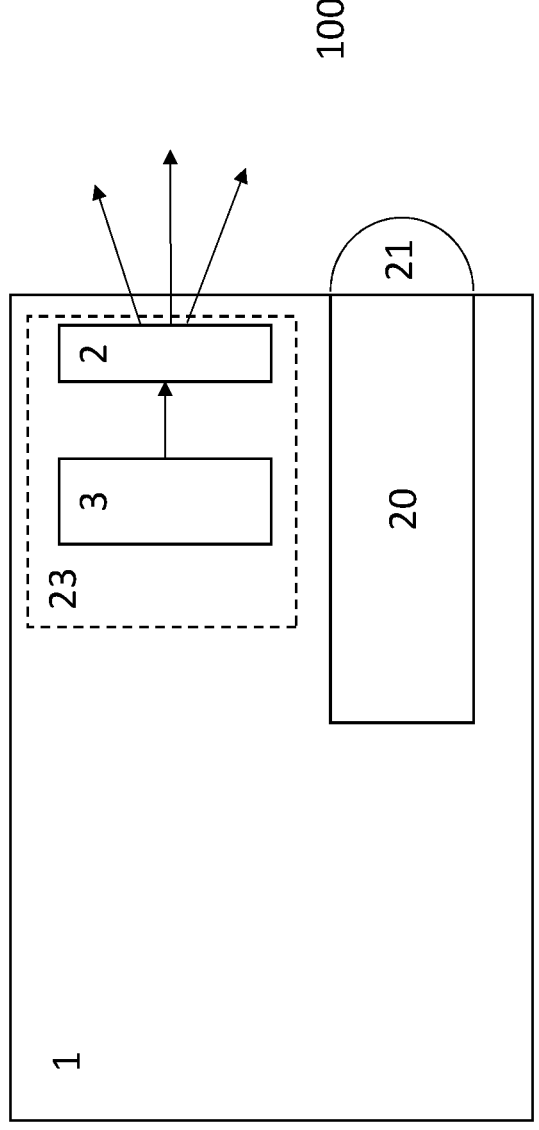
FIG. 2 shows a schematic cross-section through a rigid tip portion 1 of an endoscope.

FIG. 2 shows a schematic cross-section through a rigid tip portion 1 of an endoscope. The rigid tip portion 1 may comprise more members than those shown schematically in FIG. 2, such as a working channel 22. FIG. 2 and its description is correspondingly applicable to a capsule endoscope if not otherwise indicated or made clear from the context.

While the capsule endoscope may be used stand-alone, a proximal end of the rigid tip portion 1 is typically connected to a rigid or flexible shaft to form the endoscope. The connection may be direct or indirect via an angulation segment.

The rigid tip portion 1 comprises a light output layer 3 and a phosphor layer 2. In addition, typically, the rigid tip portion 1 may comprise an imaging system 20 including an objective lens 21 for imaging an object space 100. In FIG. 2, the object space 100 is in front of the distal end of the rigid tip portion 1 of the endoscope. However, in some embodiments, the object space 100 imaged by the imaging system 20 may be at a lateral side of the rigid tip portion 1. The object space 100 may be a cavity, e.g. a cavity in a human or animal body, or a portion of such a cavity.

Furthermore, the rigid tip portion 1 comprises an illumination system 23 including a light output layer 3 and a phosphor layer 2. The illumination system 23 is arranged to illuminate the object space 100, in particular at least a portion of the object space 100 imaged by the imaging system 20. In FIG. 2, the illumination system 23 is arranged besides the imaging system 20. However, in some embodiments, the illumination system 23 may be arranged around the imaging system 20, such that it fully or partly encircles the imaging system 20 when seen from the object space 100 (see e.g. FIGS. 5a) and b)).

Figure 5:
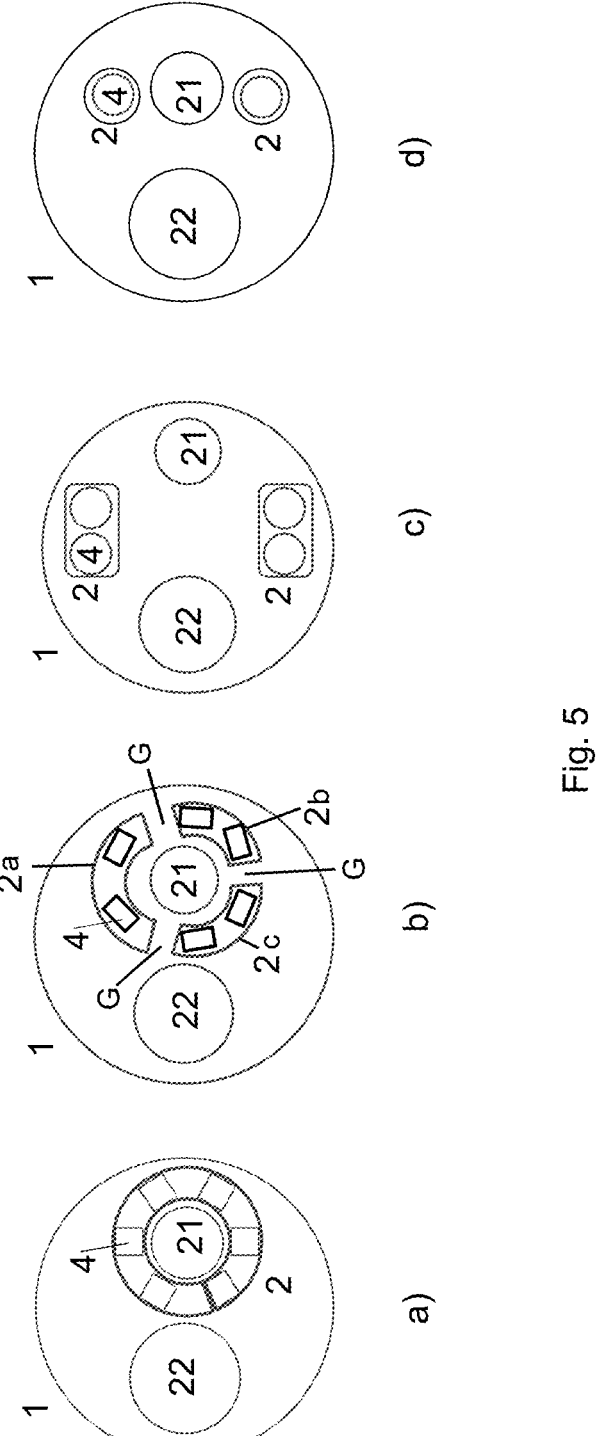
FIG. 5 shows plan views on some rigid tip portions.

FIG. 5 shows some example rigid tip portions 1 when seen in plan view from the object space 100. The phosphor layer 2 is drawn transparently such that the light output layer 3 with its light sources 4 is visible through the phosphor layer 2. As shown in FIG. 5a), the phosphor layer may be continuous such that a single portion of the phosphor layer 2 covers plural light sources 4. As shown in FIGS. 5b) to 5d), the phosphor layer 2 may be split into several portions (such as a first portion 2a, second portion 2b and third portion 2c) separated from each other by gaps G. Each portion may cover one or more light sources 4. The illumination system 23 may include a single light source 4 covered by a phosphor layer 2 (not shown in FIG. 5). The arrangement of the illumination system 23 relative to the objective lens 21 is not limited to the arrangements shown in FIG. 5, but may be varied according to the needs.

The light output layer 3 is configured to emit either first excitation light or second excitation light at a time. In some embodiments, the light output layer 3 may also emit both first excitation light and second excitation light at a time. I.e., the emission of the first excitation light (intensity of the first excitation light, at least whether or not the first excitation light is emitted at all) is controllable separately from the emission of the second excitation light (intensity of the second excitation light, at least whether or not the second excitation light is emitted at all). The endoscope system may comprise an appropriate control device.

At least in the visible spectrum (400 to 750 nm), an intensity of the first excitation light has an absolute maximum at a first peak wavelength. At least in the visible spectrum (400 to 750 nm), an intensity of the second excitation light has an absolute maximum at a second peak wavelength different from the first peak wavelength. The light output layer 3 may emit more than two different excitation lights, the intensity of each of them having an absolute maximum in the visible spectrum at a respective peak wavelength different from the peak wavelengths of the other excitation lights.

The phosphor layer 2 may cover the light output layer 3 when seen from the object space 100. The phosphor layer 2 may be in contact with the light output layer 3 including the light sources 4, as shown in the cross-section of FIG. 6b), or it may be spaced apart therefrom, as shown in FIG. 2 and in the cross-section of FIG. 6a). The phosphor layer 2 comprises one or more phosphors. The one or more phosphors may be embedded in a matrix of a material (such as a transparent resin) transparent in a wavelength range relevant for spectrum illumination and WL (i.e. typically in the visible spectrum), or the phosphor layer 2 may consist of the phosphor(s) only.

Typically, the composition of the phosphor layer 2 is substantially constant. I.e., the composition of the phosphor layer 2 integrated over the thickness of the phosphor layer 2 does not vary by more than 10% in the lateral direction. Preferably, the variation is not more than 5%, more preferably not more than 2%. Correspondingly, the composition of the phosphor layer 2 does not vary substantially in the thickness direction of the phosphor layer 2 (not more than 10%, preferably not more than 5%, more preferably not more than 2%). Typically, a thickness of the phosphor layer 2 is substantially constant (f 10%, preferably f 5%). Due to these features, manufacturing of the phosphor layer 2 is simplified.

The light (first excitation light, second excitation light) from the light output layer 3 is incident on the phosphor layer 2 and passes through the phosphor layer 2 for illuminating the object space 100, as indicated by the arrows in FIG. 2. When the light from the light output layer 3 passes through the phosphor layer 2, it excites each of the phosphors of the phosphor layer 2, e.g. by luminescence, such as fluorescence or phosphorescence. That is, each of the phosphors generates its respective first or second excited light, depending on the excitation light. Accordingly, the object space 100 is illuminated by combined light which is the excited light(s) from the one or more phosphors of the phosphor layer 2 and the remaining light from the light output layer 3 which passed through the phosphor layer 2 without exciting any excited light. Note that the light passing through the phosphor layer 2 without exciting any excited light may be scattered by the phosphor and/or by small particles (including air bubbles) if they are present in the phosphor layer 2.

The excitation lights from the light output layer 3 and the phosphor(s) of the phosphor layer 2 are configured such that each of the phosphors may be excited to generate its respective excited light by the respective peak wavelength of each of the excitation lights. For example, if the light output layer 3 emits two different excitation lights having peak wavelengths $\lambda 1$ and $\lambda 2$ and the phosphor layer 2 comprises one phosphor, the phosphor is excited by each of the peak wavelengths $\lambda 1$ and $\lambda 2$. Correspondingly, if the light output layer 3 emits two different excitation lights having peak wavelengths $\lambda 1$ and $\lambda 2$ and the phosphor layer 2 comprises two phosphors A and B, the phosphor A is excited by each of the peak wavelengths $\lambda 1$ and $\lambda 2$, and the phosphor B is excited by each of the peak wavelengths $\lambda 1$ and $\lambda 2$. The phosphor layer 2 does not comprise any phosphor which is excited by (at least) one of the excitation lights to generate respective excited light but not excited by another (at least) one of the excitation lights. Thus, none of the phosphors acts as a mere scatterer of the excitation light, and illumination efficiency is enhanced.

As outlined hereinabove, the phosphor layer 2 may additionally comprise some transparent material (such as a transparent resin) which is not excited by any of the excitation lights.

For each of the phosphors in the phosphor layer 2, the normalized spectra of the excited light generated by the different excitation lights may be different depending on the excitation wavelength. However, typically, the normalized spectra are substantially identical, independent from the excitation lights, but their absolute intensity may vary depending on the excitation light. Hence, normalization is with respect to intensity. For each of the excitation lights and each of the phosphors, an excitation ratio is defined as a ratio of an amount of the excited light generated by the excitation light to an amount of the excitation light incident on the phosphor layer 2. For each of the phosphors of the phosphor layer 2, the excitation ratio for at least one of the excitation lights is different from the excitation ratio for another one of the excitation lights. Thus, if the light output layer 3 may emit plural excitation lights at a time, for each of the excitation lights having a substantially same normalized spectrum, the ratio of excited light to the respective excitation light in the combined light may vary depending on the relative intensities of the excitation lights. That is, the spectrum of the combined light may be shaped according to the needs.

In contrast, if there is a one-to-one relationship between phosphors and excitation lights, the ratio of excited light to excitation light in the combined light is fixed.

Now, some examples of excitation lights and phosphors are described at greater detail. In this section, it is assumed that the light output layer 3 is configured to emit two different excitation lights (first excitation light having a first peak wavelength and second excitation light having a second peak wavelength). However, embodiments of the invention are not limited to just two excitation lights and may emit three or even more than three different excitation lights.

The peak wavelength of the first excitation light may be in a range of 400 nm to 430 nm. The peak wavelength of the second excitation light may be in a range of 440 nm to 480 nm. The phosphor may comprise at least one of Y3Al5O12:Ce CaSc2O4:Ce Y3(Al, Ga)5O12:Ce Lu3Al5O12:Ce Lu3(Al, Ga)5O12:Ce Y3Al5O12:Ce La3Si6N11:Ce (La, Y)3Si6N11:Ce.

The amount of Ce in these phosphors may be in the range in 0.5 wt % to 5 wt % or 0.5 mol % to 5 mol %.

Figure 3:
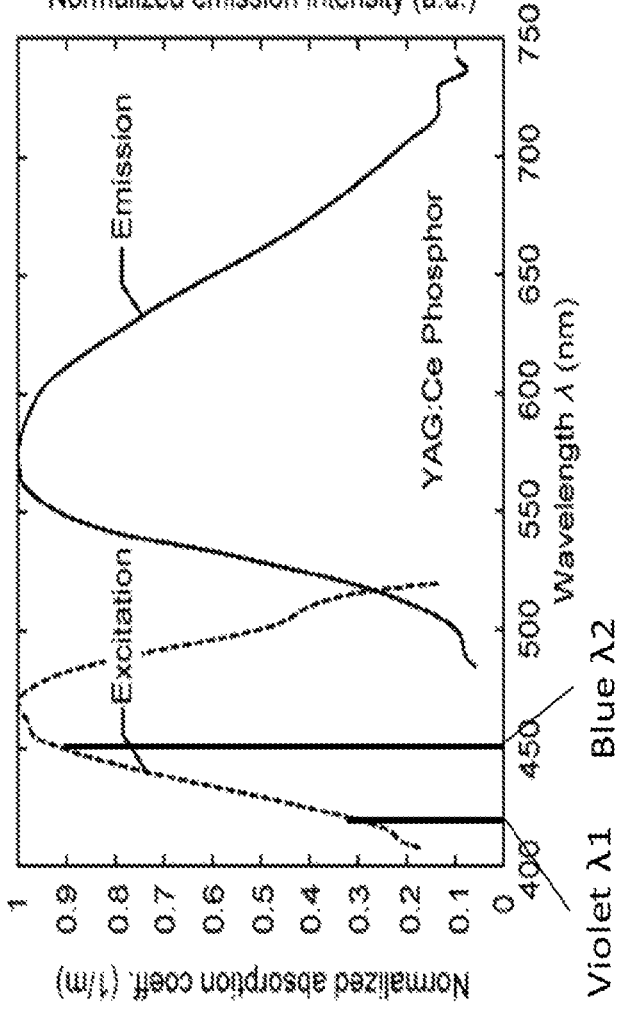
FIG. 3 shows excitation and emission spectra of Y3Al5O12:Ce (also known as YAG:Ce) phosphor.
Figure 4:
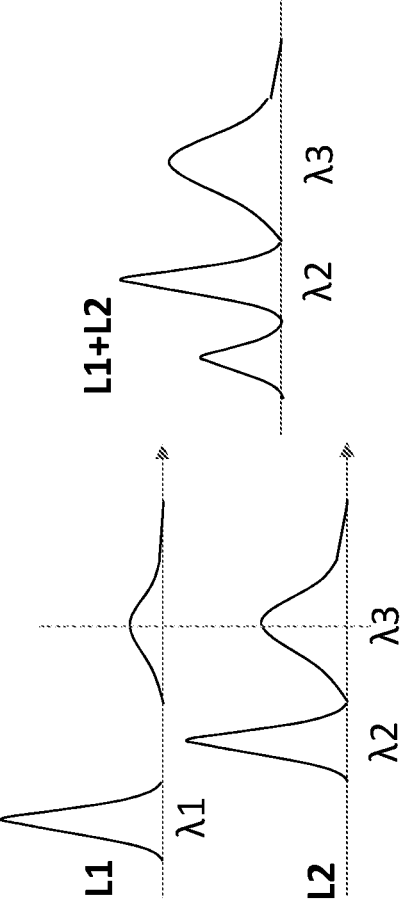
FIG. 4 illustrates schematically spectral illumination for vascular imaging and WLI according to an embodiment of the invention.

As shown in FIG. 3 for the example of Y3Al5O12:Ce (also known as YAG:Ce) as the phosphor, both violet excitation light (in the range of 400 to 430 nm) and blue excitation light (in the range of 430 to 480 nm) may excite the excited light ("Emission" in FIG. 3) having a broad spectrum around 570 nm. As shown in FIG. 4, if the violet excitation light ($\lambda 1$) excites the phosphor, the intensity of the excited light ($\lambda 3$) is rather low, and the combined light is suitable for vascular imaging (top left in FIG. 4). On the other hand, if the blue excitation light ($\lambda 2$) excites the phosphor, the intensity of the excited light is increased such that the combined light appears to be nearly white (close to the white point according to CIE 1931, bottom left in FIG. 4). If both $\lambda 1$ and $\lambda 2$ excite the phosphor, the combined light may be even closer to the white point, as shown in FIG. 4 (right).

A further improvement of WLI may be achieved if the phosphor layer 2 additionally comprises one of the following phosphors whose excited light is in the red range:

CaAlSi(ON)3:Eu

CaAlSiN3:Eu (SrCa)AlSiN3:Eu

CaAlSi(ON)3:Eu $Li_2SiN_2:Eu^{3+}$ $Sr[Mg_3SiN_4]:Eu^{2+}$ $CaAlSiN_3:Eu^{2+}$ $Li_2Ca_2[Mg_2Si_2N_6]:Eu^{2+}$ $Ca_{18.75}Li_{10.5}[Al_{39}N_{55}]:Eu^{2+}$ $Ba[Mg_3SiN_4]:Eu^{2+}$ $Sr_4[LiAl_{11}N_{14}]:Eu^{2+}$ $Ca[LiAl_3N_4]:Eu^{2+}$ $Ba[Li_2(Al_2Si_2)N_6]:Eu^{2+}$ $Sr[LiAl_3N_4]:Eu^{2+}$.

The amount of Eu in these phosphors may be in the range in 0.5 wt % to 5 wt % or 0.5 mol % to 5 mol %.

As shown in Table 1, both the violet and the blue excitation lights excite both phosphors (the phosphor of the first group and the phosphor of the second group.

TABLE 1

| | | |
|---|---|---|
| Excitation characteristics of phosphors | | |
| | wavelength $\lambda 1$ (Violet) | wavelength $\lambda 2$ (Blue) |
| Phosphor 1 (e.g. Y3Al5O12:Ce) | Yes | Yes |
| Phosphor 2 (e.g. CaAlSi(ON)3:Eu) | Yes | Yes |

Figure 10:
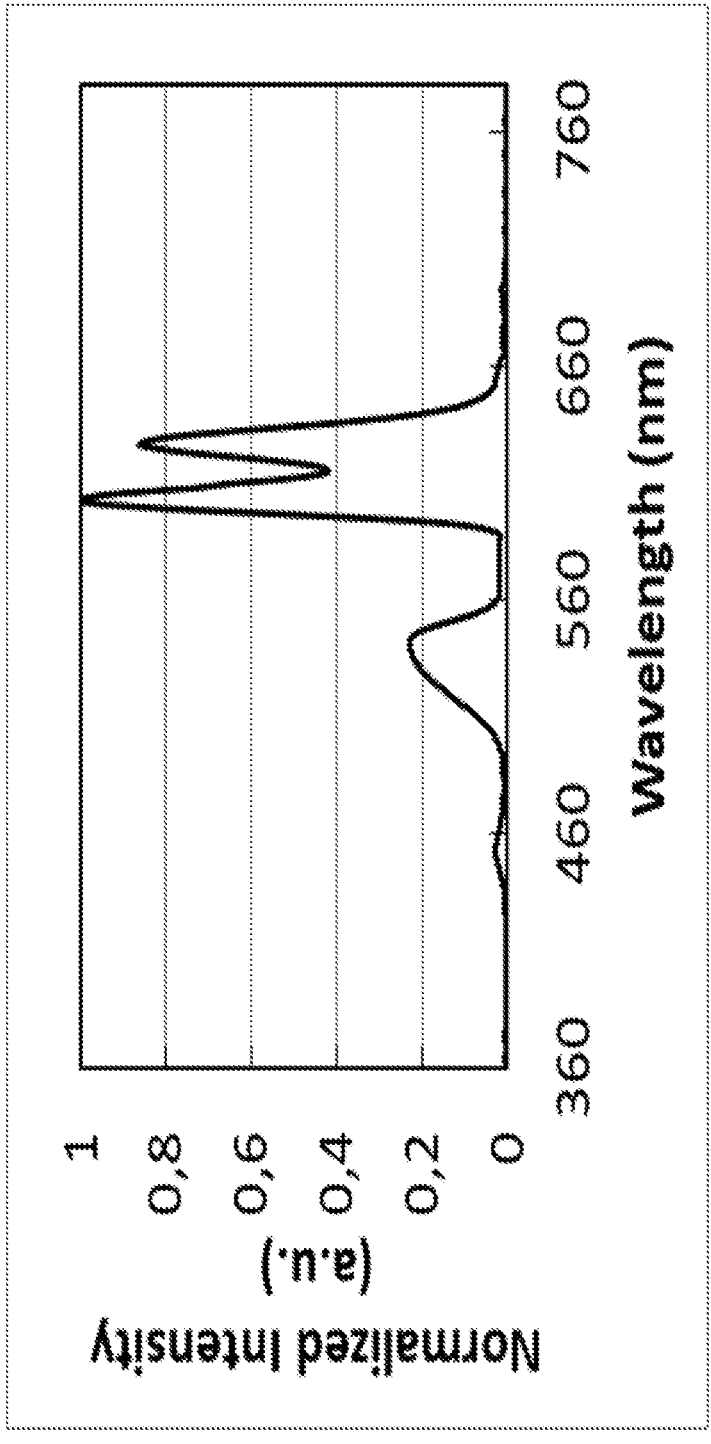
FIG. 10 shows an emission spectrum of a red phosphor.

Each of the red phosphors of the second group (i.e. CaAlSi(ON)3:Eu; CaAlSiN3:Eu; (SrCa)AlSiN3:Eu; CaAlSi (ON)3:Eu; $Li_2SiN_2:Eu^{3+}$; $Sr[Mg_3SiN_4]:Eu^{2+}$; $CaAlSiN_3$:$Eu^{2+}$; $Li_2Ca_2[Mg_2Si_2N_6]:Eu^{2+}$; $Ca_{18.75}Li_{10.5}[Al_{39}N_{55}]$: $Eu^{2+}$; $Ba[Mg_3SiN_4]:Eu^{2+}$; $Sr_4[LiAl_{11}N_{14}]:Eu^{2+}$; $Ca[LiAl_3N_4]:Eu^{2+}$; $Ba[Li_2(Al_2Si_2)N_6]:Eu^{2+}$; and $Sr[LiAl_3N_4]:Eu^{2+}$) or a combination thereof may be used not only additionally to the phosphors of the first group, but also as the only phosphor (combination) in the phosphor layer 2. If the phosphor is combined with violet (or blue) excitation light (in the wavelength ranges as described above) and green excitation light (in the wavelength range 520 nm to 590 nm), respectively, the combined light is white light and spectral illumination, as shown in FIG. 10 showing an emission spectrum of one of the red phosphors of the second group. The small amount of blue emission light may not occur for all of the phosphors.

The following conditions may apply:

the first peak wavelength differs from the second peak wavelength by at least 5 nm (preferably at least 10 nm, more preferably at least 15 nm);

a full width at half maximum of an emission spectrum of the first excitation light around the first peak wavelength is not larger than 30 nm (preferably not larger than 20 nm, more preferably not larger than 10 nm);

a full width at half maximum of an emission spectrum of the second excitation light around the second peak wavelength is not larger than 30 nm (preferably not larger than 20 nm, more preferably not larger than 10 nm).

Furthermore, one of the following conditions may apply:

the first excitation ratio is larger than the second excitation ratio by at least a factor of 2 (preferably by at least a factor of 4, more preferably by a factor of 8); and the second excitation ratio is larger than the first excitation ratio by at least a factor of 2 (preferably by at least a factor of 4, more preferably by a factor of 8).

Now, some details of the light output layer 3 will be explained.

The light output layer 3 may comprise one or more first light sources 4. Each of the first light sources 4 is configured to emit the first excitation light. Each of the one or more first light sources 4 may comprise at least one of a respective first light emitting diode and a respective first laser diode.

The light output layer 3 may comprise one or more second light sources 4. Each of the second light sources 4 is configured to emit the second excitation light 4. Each of the one or more second light sources 4 may comprise at least one of a respective second light emitting diode and a respective second laser diode.

If the light output layer 3 comprises the first and second LEDs or LDs as the light sources 4, the entire illumination system 23 may be embedded in the rigid tip portion 1. However, at least one of the first light sources 4 and the second light sources 4 may be an emission end of an optical fiber which emits excitation light from a light generation device 41 outside the rigid tip portion 1. E.g., the light generation device 41 (e.g. LED or LD) may be arranged at the proximal end of the endoscope, or in a control box of the endoscope, and the light generated by the light generation device 41 is propagated from the light generation device 41 to the light output layer 3 by one or more optical fibers 8 (or corresponding glass rods).

Figure 7:
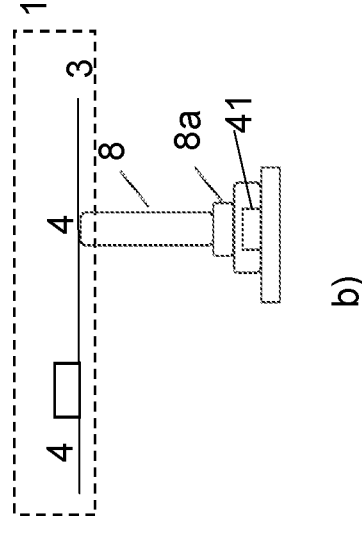
FIG. 7 shows some example illumination systems.
Figure 7:
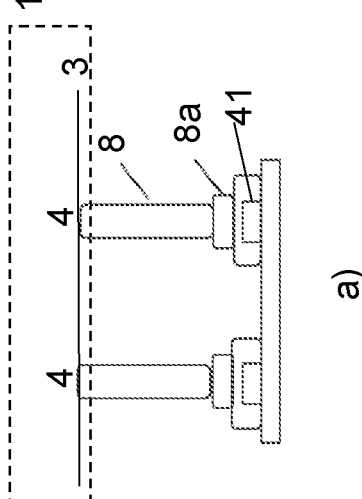
Figure 8:
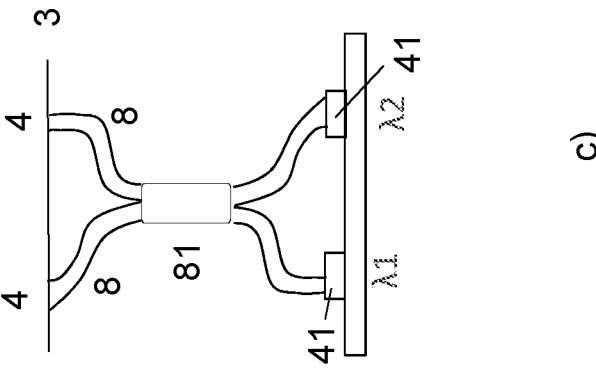
FIG. 8 shows some example illumination systems comprising optical fibers.
Figure 8:
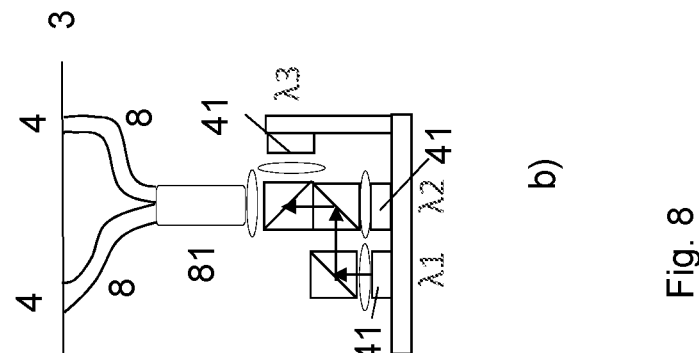
Figure 8:
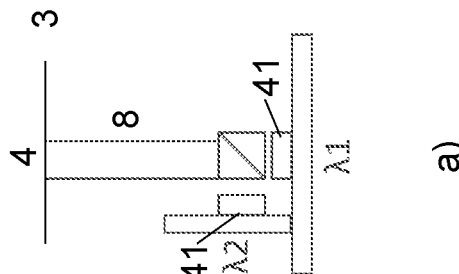

The light output layer 3 may comprise a mixture of LED(s)/LD(s) and emission end(s) of optical fiber(s) 8 ("hybrid configuration"). Such a mixture may be advantageous if sufficient space for a certain number of LED(s)/ LD(s) in the rigid tip portion 1 is not available. An example is shown in FIG. 7b). In FIG. 7b), the right light source 4 is the emission end of an optical fiber 8 emitting light from the light generation device 41 arranged at the proximal end (or outside the endoscope), while the left light source 4 is a LED or LD arranged in the rigid tip portion 1 at the distal end. If the illumination system 21 comprises plural light sources 4 emitting the first wavelength (or the second wavelength), some of them may be emission ends of optical fibers 8 and some of them may be LED/LDs arranged in the rigid tip portion 1, or all the light sources emitting one wavelength may be LEDs/LDs arranged in the rigid tip portion and all the light sources 4 emitting the other wavelength may be emission ends of optical fibers 8. While FIG. 7b) shows an example, where the light generation device 41 is directly coupled with the light source 4 in the light output layer 3, the light from plural light generation devices 41 may be combined before the light is emitted from the light sources 4 in the light output layer 3, as explained with respect to FIG. 8 further below.

In some embodiments, at least one of the one or more optical fibers may be arranged such that it emits only one of the excitation lights but not the other excitation lights. For example, the input end of the optical fibers may be connected directly to respective light generation devices emitting only the respective excitation light. This is shown in FIG. 7a. Here, the light generation devices 41 are connected to the respective optical fibers 8 by fiber connectors 8a.

In some embodiments, at least one of the one or more optical fibers may be arranged such that it may emit plural excitation lights. In this case, the excitation lights from the light generation devices may be combined by a beam combiner (shown in FIGS. 8a and 8b for two and three wavelengths, respectively) or fiber coupler (shown in FIG. 8c) before they are input into the optical fiber(s) 8 having its (their) emission end(s) in the light output layer 3. In FIG. 8b), the light from the three light generation devices 41 is split onto two optical fibers 8 by a fiber coupler/decoupler 81, such that there are two light sources 4 in the light output layer 3 in the rigid tip portion 1. Of course, the number of optical fibers 8 and light sources 4 is not limited to two but may be three or more, too. Correspondingly, instead of a beam combiner 80, a fiber coupler 81 may be used to combine the lights of plural light generation devices 41 into one or more optical fibers 8, as shown in FIG. 8c).

In some embodiments, the light output layer 3 in the rigid tip portion 1 does not comprise any LED(s)/LD(s) but only emission ends of optical fibers. In one case, the light output layer 3 does not comprise any LED/LD but a single emission end of an optical fiber as a single light source which may emit plural excitation lights.

There may be a separate portion of the phosphor layer 2 for each of the light sources (see FIG. 5d)) or jointly for several of the light sources (see FIGS. 5b) and 5c)) or even for all the light sources (see FIG. 5a)) of the light output layer 3. For example, the phosphor layer 2 may be arranged such that the first excitation light from the first light sources is incident on a first portion thereof, and the second excitation light from the second light sources is incident on a second portion thereof. The first and second portions may be separated by a gap.

The light sources of the light output layer 3 may be arranged in plural unit cells. In each of the unit cells, the light sources are arranged in a same way (e.g. respective distances, relative orientation, see e.g. FIGS. 5b) and 5c)). The excitation lights from each of the unit cells may be incident on a respective separate portion of the phosphor layer 2, or the excitation lights from plural unit cells may be incident on a common portion of the phosphor layer 2.

In some embodiments comprising emission end(s) of one or more optical fibers as light sources of the light output layer 3, the phosphor layer 2 may be arranged between the light generation devices 41 and the optical fiber(s) 8 of which the emission ends are arranged in the light output layer 3. In these embodiments, the emission end(s) of the optical fiber(s) 8 emit combined light for illuminating the object space 100 without passing through another phosphor layer 2 in the rigid tip portion 1. The same effects as described for a case where the phosphor layer 2 is arranged in the proximal end of the rigid tip portion 1 may be achieved.

FIG. 9 shows schematically the electronic configuration of example endoscopes. In FIG. 9, LDs/LEDs are arranged at light sources 4 in the rigid tip portion 1. They are controlled (i.e., at least switched on and off) by a light source control unit in the processor unit arranged outside the endoscope and connected to the proximal end thereof. The imaging system 20 provides the obtained image through an A/D converter to the image processing unit, and from there to the CPU. Typically, the A/D converter is arranged in the endoscope but it may be arranged outside in some examples. The CPU controls the image processing unit, the light source control unit and, if available, the display monitor for visualizing the image obtained by the imaging system 20.

Figure 9A:
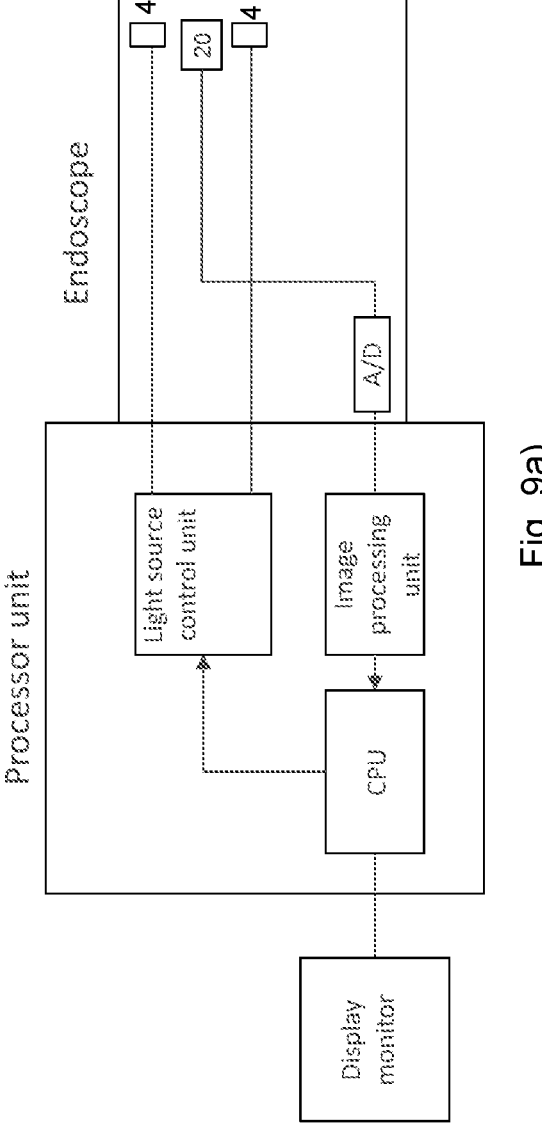
FIGS. 9a) and 9b) each show schematically the electronic configuration of example endoscopes.
Figure 9B:
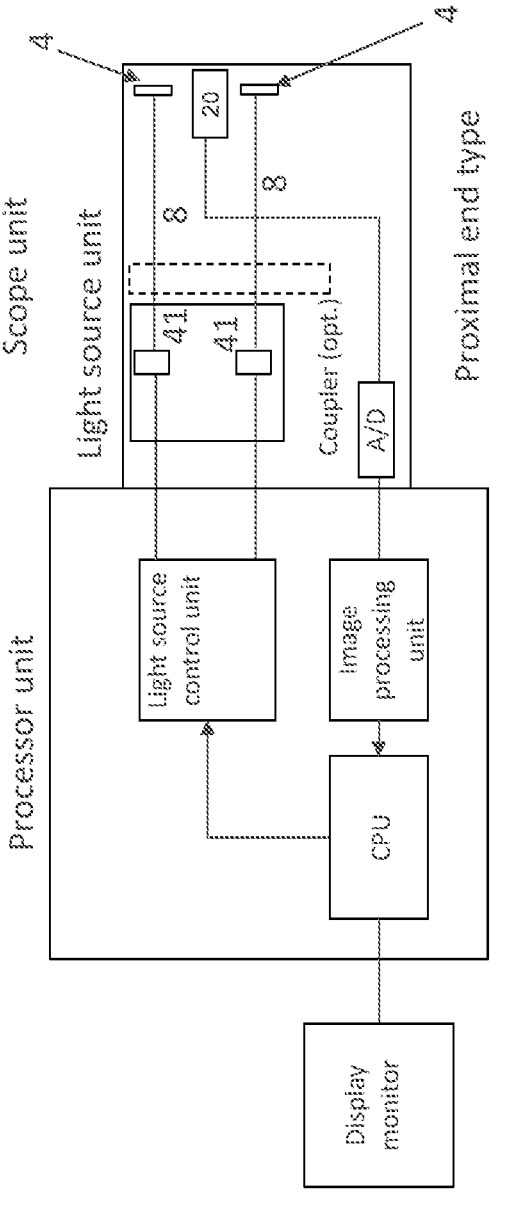

FIG. 9b) corresponds to FIG. 9a), except that light generation devices 41 (LDs/LEDs) are arranged in a light source unit arranged at (or close to) the proximal end of the endoscope and optical fibers guide the light emitted by the light generation devices 41 to their emission ends (light sources 4) in the light output layer 3. In FIG. 9b) an example is shown where each optical fiber 8 corresponds to one light generation device 41 and light source 4. Optionally, as indicated by the dashed box in FIG. 9b), the lights from different light generation devices may be coupled, as explained e.g. with respect to FIG. 8.

The invention claimed is:

1. A rigid tip portion of an endoscope or capsule endoscope, comprising
  a phosphor layer; and
  a light output layer comprising:
    a first light source comprising one of a light emitting diode or laser and configured to emit a first excitation light to illuminate an object space, through the phosphor layer, with first combined light; and
    a second light source comprising an emission end of an optical fiber and configured to emit from a light generator located outside of the light output layer a second excitation light to illuminate the object space, through the phosphor layer, with second combined light; wherein
  an intensity of the first excitation light has an absolute maximum at a first peak wavelength;
  an intensity of the second excitation light has an absolute maximum at a second peak wavelength different from the first peak wavelength;
  the phosphor layer comprises one or more phosphors;
  each of the one or more phosphors is configured to be excited by the first excitation light to generate first excited light of the respective phosphor;
  each of the one or more phosphors is configured to be excited by the second excitation light to generate second excited light of the respective phosphor;
  the first combined light comprises the first excited lights of the one or more phosphors generated by the first excitation light and remaining first excitation light passing from the light output layer through the phosphor layer without generating any excited light;

the second combined light comprises the second excited lights of the one or more phosphors generated by the second excitation light and remaining second excitation light passing from the light output layer through the phosphor layer without generating any excited light.

2. The rigid tip portion of an endoscope or capsule endoscope according to claim 1, wherein the phosphor layer does not comprise any phosphor configured to be excited by one of the first and second excitation lights to generate respective excited light and configured such that it does not generate the respective excited light if it is excited by the other one of the first and second excitation lights.

3. The rigid tip portion of an endoscope or capsule endoscope according to claim 1, wherein for each of the one or more phosphors:

a ratio of an amount of the respective first excited light generated by the first excitation light to an amount of the first excitation light incident on the phosphor layer is a first excitation ratio of the respective phosphor;

a ratio of an amount of the respective second excited light generated by the second excitation light to an amount of the second excitation light incident on the phosphor layer is a second excitation ratio of the respective phosphor;

the first excitation ratio of the respective phosphor is different from the second excitation ratio of the respective phosphor.

4. The rigid tip portion of an endoscope or capsule endoscope according to claim 3, wherein either the first excitation ratio is larger than the second excitation ratio by at least a factor of 2; or the second excitation ratio is larger than the first excitation ratio by at least a factor of 2.

5. The rigid tip portion of an endoscope or capsule endoscope according to claim 1, wherein at least one of the first peak wavelength differs from the second peak wavelength by at least 5 nm;

a full width at half maximum of an emission spectrum of the first excitation light around the first peak wavelength is not larger than 15 nm; and a full width at half maximum of an emission spectrum of the second excitation light around the second peak wavelength is not larger than 10 nm.

6. The rigid tip portion of an endoscope or capsule endoscope according to claim 1, wherein at least one of the first peak wavelength is in a range of 400 nm to 430 nm; and the second peak wavelength is in a range of 430 nm to 480 nm.

7. The rigid tip portion of an endoscope or capsule endoscope according to claim 1, wherein the phosphor comprises at least one of Y3Al5O12:Ce CaSc2O4:Ce Y3(Al,Ga)5O12:Ce Lu3Al5O12:Ce Lu3(Al,Ga)5O12:Ce Y3Al5O12:Ce La3 Si6N11:Ce (La,Y)3Si6N11:Ce.

8. The rigid tip portion of an endoscope or capsule endoscope according to claim 1, wherein the phosphor comprises at least one of CaAlSi(ON)3:Eu CaAlSiN3:Eu (SrCa)AlSiN3:Eu CaAlSi(ON)3:Eu $Li_2SiN_2:Eu^{3+}$ $Sr[Mg_3SiN_4]:Eu^{2+}$ $CaAlSiN_3:Eu^{2+}$ $Li_2Ca_2[Mg_2Si_2N_6]:Eu^{2+}$ $Ca_{18.75}Li_{10.5}[Al_{39}N_{55}]:Eu^{2+}$ $Ba[Mg_3SiN_4]:Eu^{2+}$ $Sr_4 [LiAl_{11}N_{14}]:Eu^{2+}$ $Ca[LiAl_3N_4]:Eu^{2+}$ $Ba[Li_2 (Al_2Si_2)N_6]:Eu^{2+}$ $Sr[LiAl_3N_4]:Eu^{2+}$.

9. The rigid tip portion of an endoscope or capsule endoscope according to claim 8, wherein one of the first peak wavelength and the second peak wavelength is in a range of 520 nm to 590 nm.

10. The rigid tip portion of an endoscope or capsule endoscope according to claim 1, wherein the first light source comprises plural first light sources each configured to emit the first excitation light;

the second light source comprises plural second light sources each configured to emit the second excitation light;

the phosphor layer comprises a first portion arranged such that the first excitation light from the first light sources is incident on the first portion;

the phosphor layer comprises a second portion arranged such that the second excitation light from the second light sources is incident on the second portion;

the first portion is separated from the second portion by a gap.

11. The rigid tip portion of an endoscope or capsule endoscope according to claim 1, wherein the first light source comprises plural first light sources each configured to emit the first excitation light;

the second light source comprises plural second light sources each configured to emit the second excitation light;

at least some of the first light sources and the second light sources are arranged in plural unit cells;

in each of the unit cells, the respective second light source is arranged relative to the respective first light source in a same way.

12. The rigid tip portion of an endoscope or capsule endoscope according to claim 11, wherein the phosphor layer comprises a third portion arranged such that the first and second excitation lights from the first and second light sources of at least one of the unit cells is incident on the third portion;

the third portion is separated from a remainder of the phosphor layer by a gap.

13. The rigid tip portion of an endoscope or capsule endoscope according to claim 1 phosphor layer is continuous.

14. The rigid tip portion of an endoscope or capsule endoscope according to claim 1, wherein either the phosphor layer is in contact with the light output layer and covers the light output layer; or the phosphor layer is spaced apart from the light output layer.

15. The rigid tip portion of an endoscope or capsule endoscope according to claim 1, further comprising an objective lens configured to image at least a portion of the object space.

16. The rigid tip portion of an endoscope or capsule endoscope according to claim 1, further comprising a processor configured to separately control the intensity of the first excitation light from the intensity of the second excitation light.

17. The rigid tip portion of an endoscope or capsule endoscope according to claim 1, wherein a normalized spectrum of the first excited light is the same as a normalized spectrum of the second excited light.

18. An endoscope comprising the rigid tip portion of the endoscope according to claim 1 and a flexible or rigid shaft connected directly or indirectly with a proximal end of the rigid tip portion.

19. An endoscope system, comprising:

a rigid tip;

a flexible or rigid shaft connected directly or indirectly with a proximal end of the rigid tip;

a first light source in the rigid tip and comprising one of a light emitting diode or laser and configured to emit a first excitation light;

a second light source in the rigid tip comprising an emission end of an optical fiber and configured to emit from a light generator located outside of the rigid tip a second excitation light;

a phosphor layer comprising one or more phosphors; wherein the first light source is arranged such that the first excitation light is incident on the phosphor layer;

the second light source is arranged such that the second excitation light is incident on the phosphor layer;

an intensity of the first excitation light has an absolute maximum at a first peak wavelength;

an intensity of the second excitation light has an absolute maximum at a second peak wavelength different from the first peak wavelength;

each of the one or more phosphors is configured to be excited by the first excitation light to generate first excited light of the respective phosphor;

each of the one or more phosphors is configured to be excited by the second excitation light to generate second excited light of the respective phosphor;

the first light source is configured to propagate a first combined light to a distal end of the rigid tip;

the optical fiber is configured to propagate a a second combined light to the emission end of the optical fiber;

the emission end of the optical fiber is configured to illuminate an object space;

the first combined light comprises the first excited lights of the one or more phosphors generated by the first excitation light from the first light source and remaining first excitation light passing from the light source through the phosphor layer without generating any excited light;

the second combined light comprises the second excited lights of the one or more phosphors generated by the second excitation light from the light source and remaining second excitation light passing from the light source through the phosphor layer without generating any excited light.

20. The endoscope system according to claim 19, wherein for each of the one or more phosphors:

a ratio of an amount of the respective first excited light generated by the first excitation light to an amount of the first excitation light incident on the phosphor layer is a first excitation ratio of the respective phosphor;

a ratio of an amount of the respective first excited light generated by the second excitation light to an amount of the second excitation light incident on the phosphor layer is a second excitation ratio of the respective phosphor;

the first excitation ratio of the respective phosphor is different from the second excitation ratio of the respective phosphor.

21. The endoscope system according to claim 19, wherein a normalized spectrum of the first excited light is the same as a normalized spectrum of the second excited light.

*    *    *    *    *